(12) United States Patent
Kim et al.

(10) Patent No.: US 10,458,970 B2
(45) Date of Patent: Oct. 29, 2019

(54) METHOD AND APPARATUS FOR DETECTING CONTAMINANTS IN WATER

(71) Applicants: Tae Yong Kim, Gwangju (KR); Sungyong In, Germantown, MD (US)

(72) Inventors: Tae Yong Kim, Gwangju (KR); Sungyong In, Germantown, MD (US)

(73) Assignee: Sungyong In, Germantown, MD (US)

( * ) Notice: Subject to any disclaimer, the term of this patent is extended or adjusted under 35 U.S.C. 154(b) by 3 days.

(21) Appl. No.: 15/493,113

(22) Filed: Apr. 20, 2017

(65) Prior Publication Data

US 2017/0307580 A1    Oct. 26, 2017

Related U.S. Application Data

(60) Provisional application No. 62/324,930, filed on Apr. 20, 2016.

(30) Foreign Application Priority Data

Mar. 3, 2017   (KR) .................. 10-2017-0027854

(51) Int. Cl.
*G01N 33/18* (2006.01)
*G01N 21/53* (2006.01)
(Continued)

(52) U.S. Cl.
CPC .......... *G01N 33/1893* (2013.01); *G01N 21/41* (2013.01); *G01N 21/53* (2013.01);
(Continued)

(58) Field of Classification Search
CPC ........ G01N 21/41; G01N 21/53; G01N 21/94; G01N 27/08; G01N 33/1813; G01N 33/1826; G01N 33/1893; Y02A 20/206
See application file for complete search history.

(56) References Cited

U.S. PATENT DOCUMENTS

3,710,111 A * 1/1973 Collura .................. G01N 21/33
                                                              250/373
4,622,465 A * 11/1986 Harig .................. G01N 33/1833
                                                              250/301
(Continued)

*Primary Examiner* — Randy W Gibson
*Assistant Examiner* — Gedeon M Kidanu
(74) *Attorney, Agent, or Firm* — Ichthus International Law PLLC (57) ABSTRACT

The present disclosure relates to an apparatus or methodology for detecting one or more contaminants and/or measuring watering quality in a water supply system, which may be installed at any place chosen by a user so as to detect the one or more contaminants and/or measure the quality of water flowing through a pipe of the water supply system, such as tap water, water purifier, drinking water storage facility, or water intake facility. The present disclosure provides numerous benefits over the existing technology including convenience of handling with ease and safe fastening and installment of the apparatus for detecting one or more contaminants and/or measuring quality of water. Furthermore, the present technology enables the monitoring of the contamination level of the water delivered in the water supply system at any time chosen by the user because the contamination can be detected and/or the water quality can be measured and monitored in a wireless environment either continuously or intermittently through a wireless communication system with a remote user device.

6 Claims, 9 Drawing Sheets

(51) Int. Cl.
*G01N 27/08* (2006.01)
*G01N 21/41* (2006.01)
*G01N 21/94* (2006.01)
*G01N 15/06* (2006.01)

(52) U.S. Cl.
CPC ............ *G01N 21/94* (2013.01); *G01N 27/08* (2013.01); *G01N 33/1813* (2013.01); *G01N 33/1826* (2013.01); *G01N 15/0656* (2013.01); *Y02A 20/206* (2018.01)

(56) References Cited

U.S. PATENT DOCUMENTS

| | | | | |
|---|---|---|---|---|
| 5,315,243 | A * | 5/1994 | Kempster | G01N 15/0656 324/204 |
| 5,811,664 | A * | 9/1998 | Whittington | G01N 15/0656 73/53.07 |
| 6,707,048 | B2 * | 3/2004 | Hallett | A61L 2/10 210/748.1 |
| 8,582,100 | B1 * | 11/2013 | Tucker | G01N 15/0227 356/335 |
| 2007/0064218 | A1 * | 3/2007 | Montgomery | G01F 1/661 356/28 |
| 2012/0248779 | A1 * | 10/2012 | Hama | F03B 17/06 290/54 |
| 2014/0009621 | A1 * | 1/2014 | Tucker | G01N 15/0227 348/159 |
| 2014/0077497 | A1 * | 3/2014 | Letang | F03B 13/00 290/54 |

\* cited by examiner

METHOD AND APPARATUS FOR DETECTING CONTAMINANTS IN WATER

CROSS-REFERENCE TO RELATED APPLICATION(S)

This application claims priority from U.S. Provisional Application No. 62/324,930, titled "Apparatus for Measuring Water Quality," filed Apr. 20, 2016, and from Korean Patent Application No. 10-2017-0027854, titled "Device for Measuring Water Quality," filed Mar. 3, 2017, the entire contents of which are incorporated herein in their entirety.

TECHNICAL FIELD

The present disclosure relates to a device and/or apparatus for detecting contaminants in water by measuring water quality; more specifically, it relates to a measuring device or apparatus coupled between two adjacent pipes forming a continuous section to detect the contaminant in the fluid flowing through the pipe.

BACKGROUND

Currently, with the soaring demand for high quality tap water caused by ever increasing population in urban areas, which is propelled by a high population growth and industrialization of society, a shortage of high quality water has become an increasingly serious problem. Moreover, increasing difficulties in securing a quality water source due to deteriorating water quality and polluted environments around the water supply pipelines installed in the urban areas are aggravating the water quality deterioration within a water supply system including pipelines.

In general, water from a raw water source supplied to a water treatment facility is purified in the water treatment facility and supplied to households. The length of the pipelines supplying water from the water treatment facility to faucets of each household amounts to tens of kilometers, and the water is at risk of contamination while passing through these long pipelines in the water supply system. Consequently, many households tend to distrust the quality of tap water.

What is more, water quality data are processed manually at each water quality measurement point, and incorrect data inputs can result from manual processing.

For these reasons, a device for measuring water quality has been developed, and in the related art, a document entitled "the water quality analysis system weighing and reaction device," Patent No. 10-0754853 registered in South Korea, a weighing and reaction device for water quality analysis system, which is carried to a place requiring water quality analysis, was disclosed.

However, the existing water quality analysis system by means of a weighing and reaction device requires a cumbersome procedure with considerable personnel costs and hours of work because the device has to be carried to a scheduled place and installed each time and that water samples need to be taken for analysis.

To address this and other problems, there is a need for a more efficient and improved methodology and apparatus with a simple structure that can detect contaminants and monitor water quality in a fluid flowing path in a transport pipe without the need to sample the fluid to be analyzed.

SUMMARY

In response to this need, the present disclosure addresses the above-described problems, resulting in a water quality measurement device that is capable of selective measurements for water contamination monitoring through a simple installation of the present technology along a pipeline joint, to detect and measure the quality of the fluid flowing through it, such as a water supply pipeline, water purifier, or drinking water storage facility.

In an aspect of the present disclosure, an embodiment provides a water quality measurement device or apparatus. The apparatus is configured to detect contaminants in water flowing in a pipe. The apparatus includes a first pipe and a second pipe configured to transport the water, and a flow tube disposed between the first pipe and the second pipe joining the two pipes into a continuous section for transporting the water. The flow tube includes an optical sensor and an electricity conductivity sensor. The optical sensor is configured to detect one or more biological contaminants in the water flowing inside the flow tube, and the electricity conductivity sensor is configured to detect one or more metallic components in the water flowing inside the flow tube. In an aspect of the present disclosure, the apparatus may further include one or more coupling units configured to couple the first pipe, the flow tube, and the second pipe into the continuous section for transporting the water.

In an aspect of the present disclosure, the flow tube may include a transparent portion enabling a direct view from outside for visual inspection and monitoring of the water flowing inside the flow tube.

In another aspect of the present disclosure, the optical sensor may include a light source configured to emit light into the water flowing inside the flow tube, and a photodetector configured to receive the emitted light from the light source. The photodetector is disposed and is configured to face the light source inside the flow tube.

In another aspect of the present disclosure, the electricity conductivity sensor may include a plurality of electrodes including an anode and a cathode installed diametrically opposite in the flow tube, and an electrical conductivity meter configured to measure a voltage or a current across the plurality of electrodes for determining a presence of one or more metallic components in the water flowing inside the flow tube.

In an aspect of the present disclosure, the energy harvesting unit includes one or more turbine blades disposed inside the flow tube, and a power generation unit coupled to the one or more turbine blades and configured to transform a rotary movement of the one or more turbine blades to electric energy.

In an aspect of the present disclosure, the energy harvesting unit is configured to supply power to the optical sensor and the electrical conductivity sensor for operation.

As such, the present technology offers numerous benefits including user convenience because it can detect the contaminants in the water, by measuring water quality after being installed in a place selected by the user without having the need for sampling the water flowing through the pipe of a system such as tap water, water purifier, drinking water storage facility, or water intake facility.

Further, it also enables the monitoring of the contamination levels of the water flowing through the pipe any time chosen by the user, because the present technology provides means for detecting one or more contaminants by measuring the water quality of the water flowing through the pipe continuously or intermittently. Another advantage of the present technology is superior safety and convenience owing to its easy and safe handling without using any tools for detecting one or more contaminants and measuring the quality of water in a water supply system.

BRIEF DESCRIPTION OF DRAWINGS

A more detailed understanding may be obtained from the following description in conjunction with the following accompanying drawings.

DETAILED DESCRIPTION

The device for detecting one or more contaminants and/or measuring water quality according to the present technology is described in detail below with reference to the attached drawings.

It should be noted that, in adding the reference numerals to the components of each drawing, care has been taken to use the same numerals for the same components even though they appear in different drawings. It should also be noted that, in describing the present technology, a detailed explanation of a related configuration or unction already well-known will be omitted if such a detailed explanation is considered to unnecessarily obscure the gist of the present technology.

In explaining the present disclosure, terms such as first, second, A, B, (a), and (b) may be used. These terms are used to distinguish a part (or a subcomponent) of a component from other parts of the component, and they do no limit the nature, order, or sequence of the corresponding component per se. When a component is described to be "coupled," "combined," or "joined," it is understood that the component is coupled or joined to another component, or its subcomponents are coupled or joined with each other.

Figure 1:
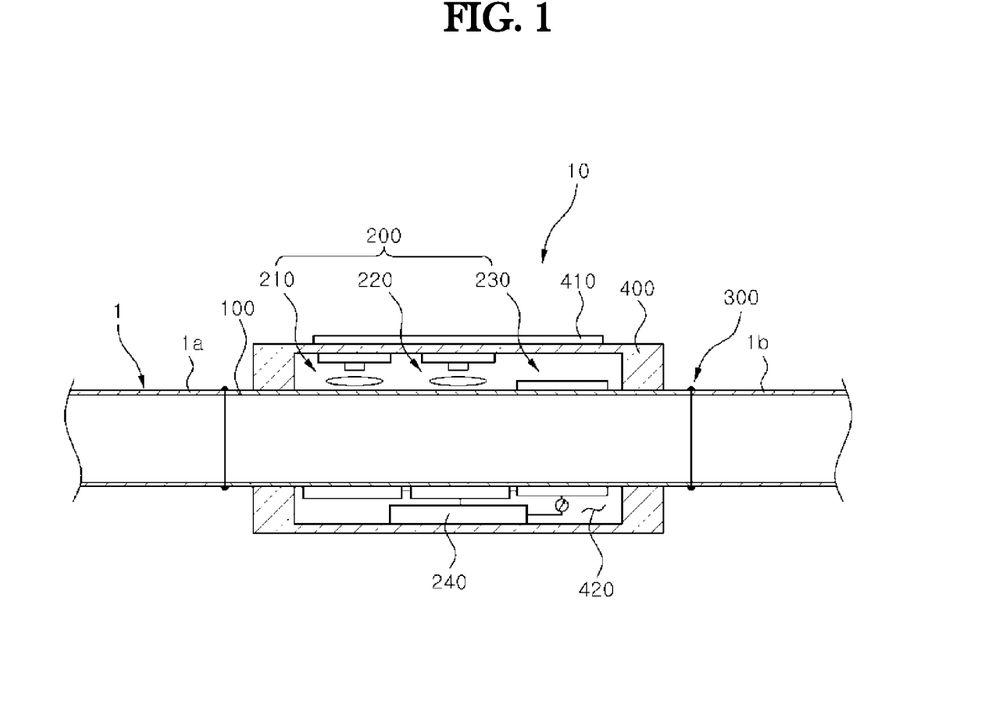
FIG. 1 illustrates an example of a device for measuring water quality according to an aspect of the present disclosure.
Figure 2:
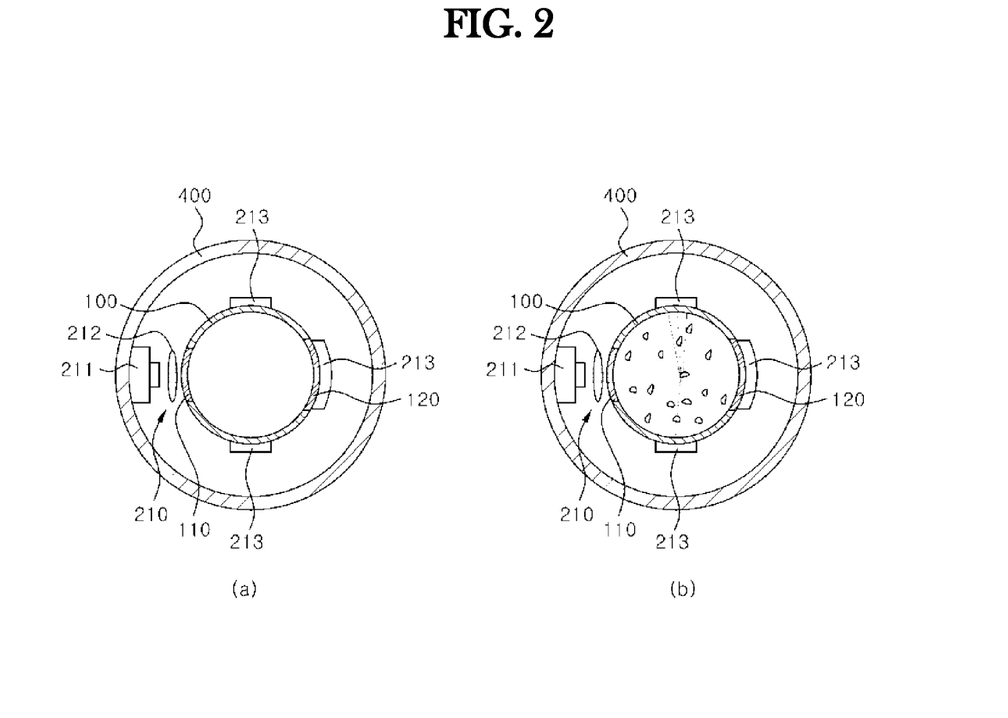
FIG. 2 illustrates an example of an optical sensor in accordance with an aspect of the present disclosure.
Figure 3:
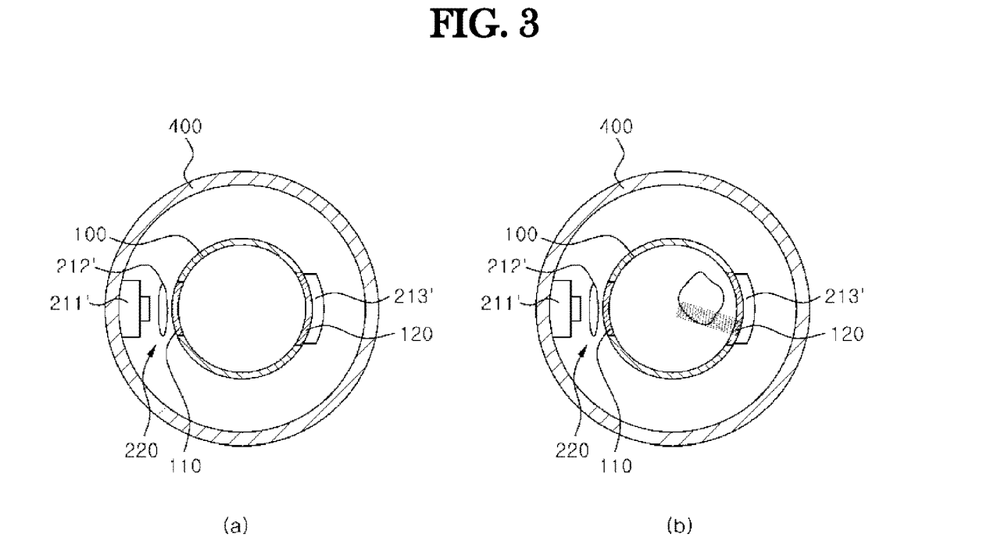
FIG. 3 illustrates an example of a photorefractive sensor in accordance with an aspect of the present disclosure.
Figure 4:
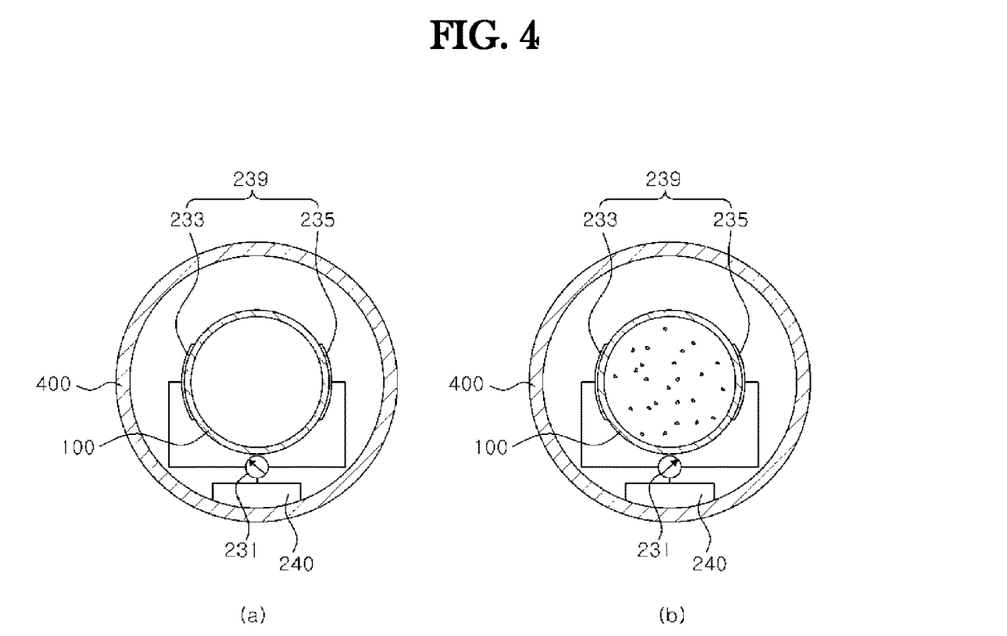
FIG. 4 illustrates an example of an electrical conductivity sensor in accordance with an aspect of the present disclosure.
Figure 5A:
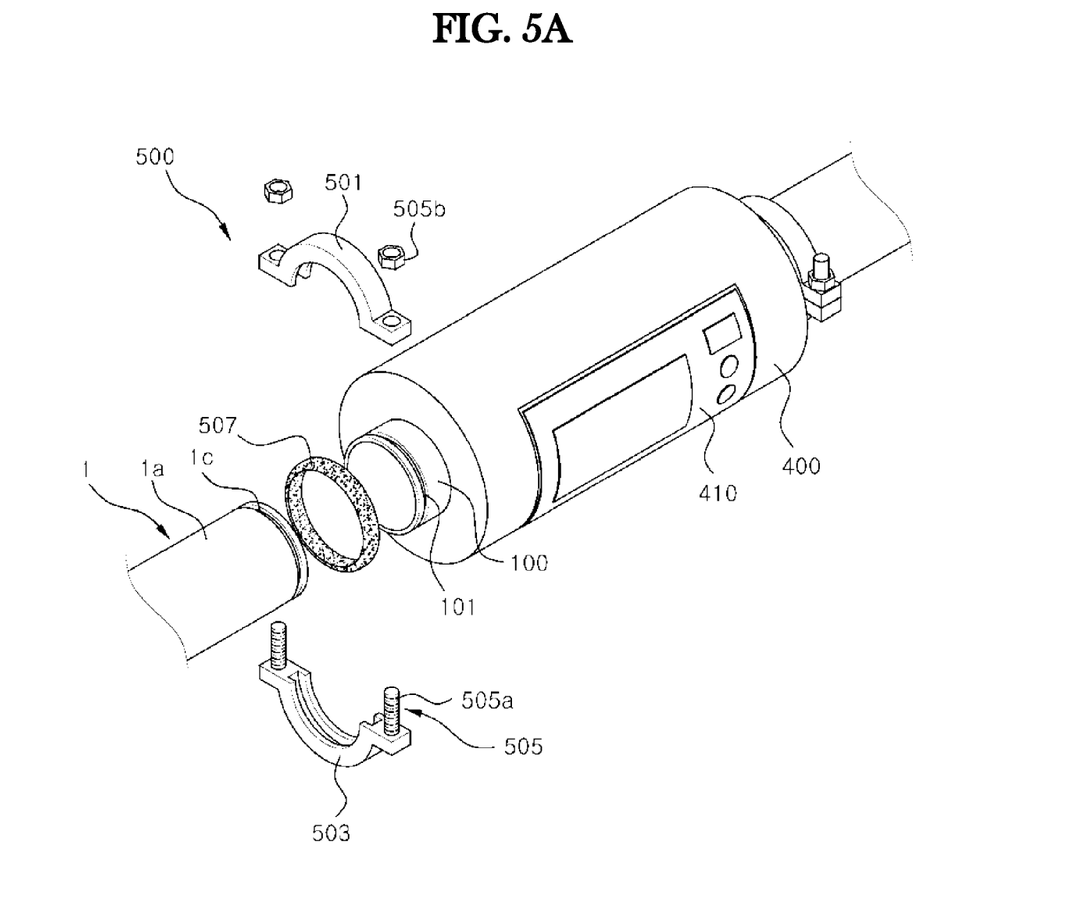
FIGS. 5A and 5B illustrate an exemplary embodiment, in accordance with an aspect of the present disclosure.
Figure 5B:
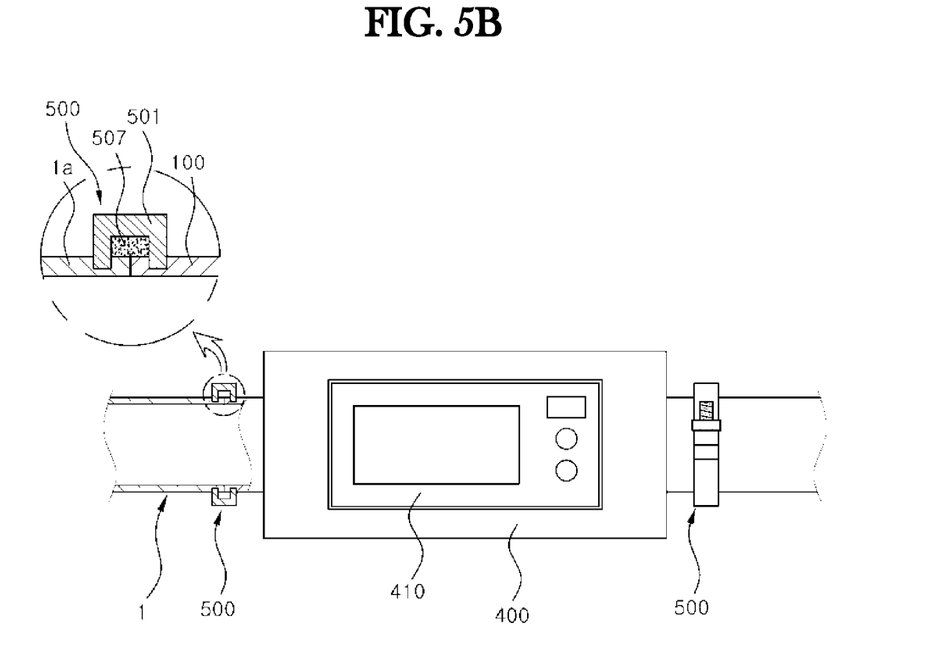
Figure 6A:
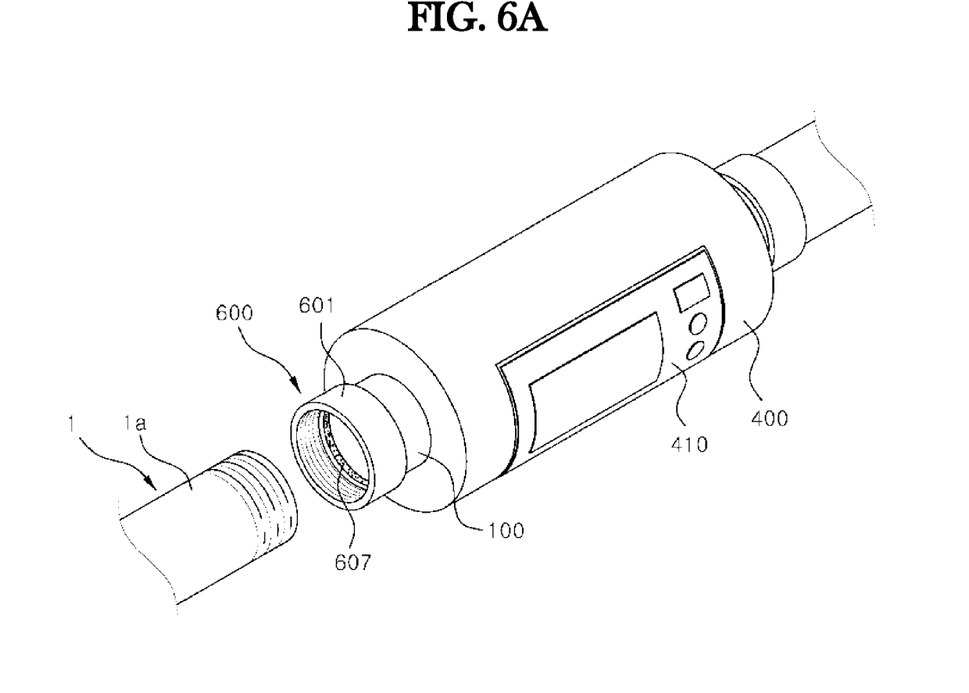
FIGS. 6A and 6B illustrate another embodiment, in accordance with an aspect of the present disclosure.
Figure 6B:
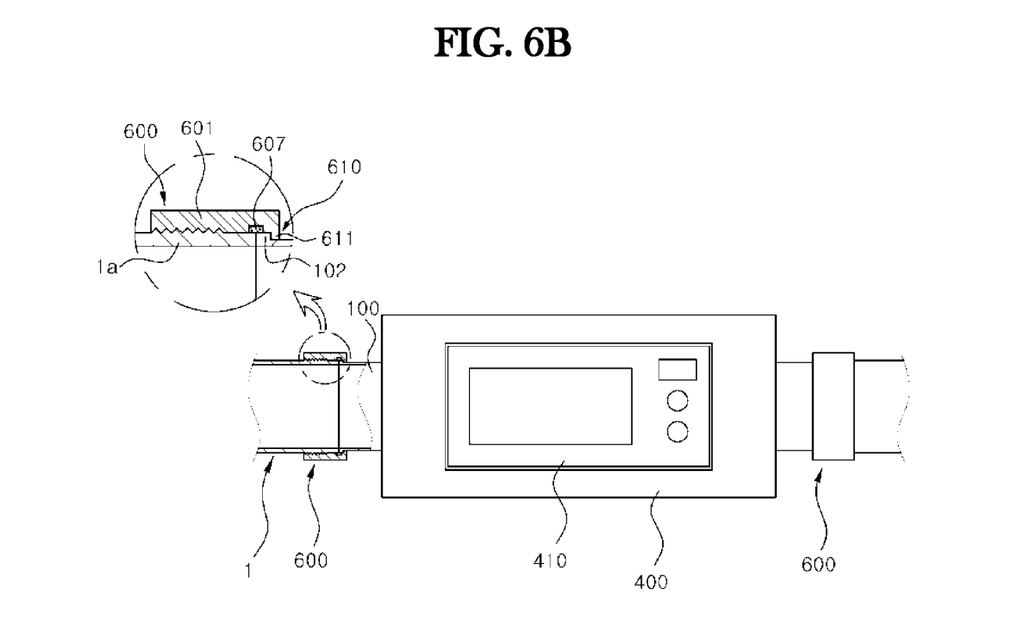
Figure 7:
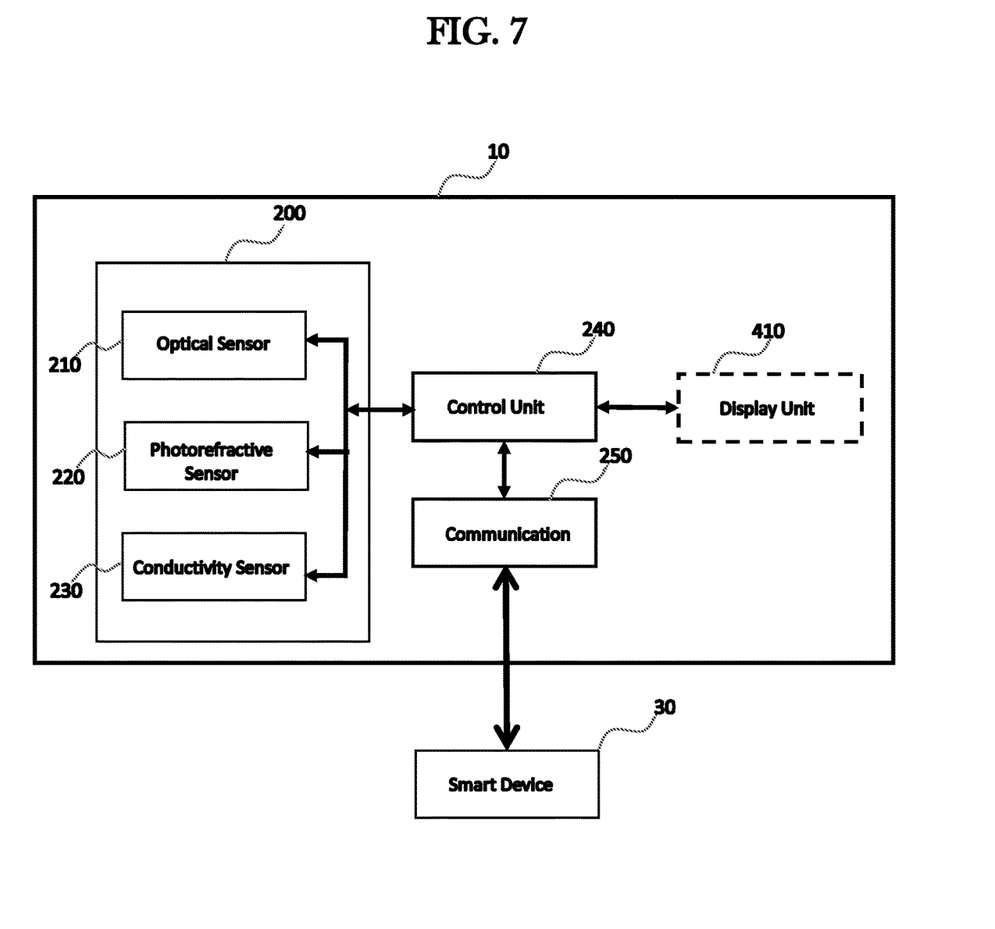
FIG. 7 is a block diagram of the device for measuring water quality in accordance with an aspect of the present disclosure.

FIG. 1 is a drawing illustrating an example of a device for detecting one or more contaminants and/or measuring water quality according to an aspect of the present disclosure. FIG. 2 is a drawing illustrating an example of an optical sensor according to FIG. 1. FIG. 3 is a drawing illustrating an example of a photorefractive sensor according to FIG. 1. FIG. 4 is a drawing illustrating an example of an electrical conductivity sensor according to FIG. 1. FIGS. 5a and 5b are drawings illustrating an exemplary embodiment in which the present technology is coupled to adjacent pipes in an aspect of the present disclosure. FIGS. 6a and 6b are drawings illustrating another embodiment in which the present technology is coupled to adjacent pipes in an aspect of the present disclosure. FIG. 7 is a block diagram of the device for detecting one or more contaminants and/or measuring water quality according to another embodiment of the present disclosure.

By way of example, an example embodiment of a device for detecting one or more contaminants and/or measuring water quality (10) is described below in reference to these drawings.

In FIG. 1, the device for detecting one or more contaminants and/or measuring water quality (10) includes the following parts: a flow tube (100) coupled between the adjacent pipes (1); a sensor unit (200) that is extrapolated to the flow tube (100) to measure the quality of the fluid passing through the flow tube (100); and a coupling unit (300) that couples the adjacent pipes (1) to the flow tube (100).

First, the flow tube (100) may be configured such that one of its two ends is coupled to the opening of one pipe (1a) of the two adjacent pipes (1) and the other end is coupled to the opening of the other pipe (1b). As such, the flow tube (100) maintains the flow path of the liquid flowing through the adjacent pipes (1) and can discharge the fluid flowing into one end to the other. The flow tube (100) may also be configured in a manner to provide a direct view from the outside. In one implementation, the flow tube (100) may be constructed partially or entirely with a transparent material so that the inside of the flow tube (100) can be viewed from the outside.

The flow tube (100) may also include a transparent window (110) to have the light from the light source (211) pass into the inside of the flow tube (100) and a window for the photodetector (120) to have the light pass from the inside of the flow tube (100) towards an optical sensor (e.g., a photodetector 213), as shown in FIG. 2.

Next, the sensor unit (200) may include a light source (211) that emits light into the flow tube (100); and a photodetector (213) that is positioned around the flow tube (100) to face the light source (211) to receive the emitted light from the sensor unit (200).

Thus, the sensor unit (200) can also be used as an optical sensor (210) or a photorefractive sensor (220), with the same components, depending on the amount and refraction of light. As illustrated in FIG. 2, the optical sensor (210) may include a photodetector (213) and additionally include an optical system (212) to detect the light emitted from the light source (211) with more efficacy.

Here, the optical sensor (210), which may be configured to detect biological contaminants such as micro-organisms, uses a light emitting diode (LED) or laser diode (LD) as the light source (211) emitting light beams of wavelength 860 nm (±30 nm).

On the other hand, the light emitted from the light source (211) to the optical sensor (210) may pass through the optical system (212) and the flow tube (100) with a fluid flowing through it and enters the photodetector (213). In this process, the fluid flowing through the flow tube (100) is subject to inspection to determine whether it is contaminated with biological contaminants or not.

More specifically, if any biological contaminants are present in the fluid, the biological contaminants will scatter the light emitted from the light source (211), which is then detected by the photodetector (213), by means of an amount of light entering the photodetector (213), thus enabling the measurement necessary for determining whether or not the fluid flowing through the flow tube (100) is contaminated.

Optionally, multiple photodetectors (213) may be installed to increase the efficacy in detection of the light scattered by the contaminants.

As illustrated in FIG. 3, the photorefractive sensor (220) may include a light source (211') and a photodetector (213'), but can additionally include an optical system (212') to detect the light emitted from the light source (211') with a higher efficacy.

The photorefractive sensor (220) can measure the contaminants or other solutions (organic and/or inorganic materials dissolved) other than the fluid flowing through the flow tube (100). An LED or LD light source can be used as the light source (211'), and a charge-coupled device (CCD) can be used as the photodetector (213').

From an operational perspective, the light emitted from the light source (211') to the optical sensor (210) passes through the optical system (212') and the flow tube (100') with the fluid flowing through it and enters the photodetector (213').

Here, in this example, the light emitted from the light source (211'), while being emitted to the photodetector (213') after passing through the optical system (212'), may have a refractive index different from that of an intrinsic refractive index of the fluid without other foreign solution (s), flowing in the flow tube (100), because of an encounter with a different medium with a different refractive index due to the presence of foreign solutions (materials) or contaminants in the fluid.

In an aspect of the present disclosure, as shown in FIGS. 3(a) and 3(b) a level of contamination of the fluid, e.g., one or more solution(s) other than the water, flowing in the flow tube (100), may be determined by detecting and/or determining a focal shift of the light detected with respect to its usual position due to refraction caused by the one or more solutions or contaminants contained in the solutions, when the light emitted from the light source (211') enters the photodetector (213').

In the example, as mentioned above, the light source may include either a light emitting diode (LED) or a laser diode (LD) having different characteristics. Both LED and LD light sources may be characterized in terms of coherence, bandwidth and direction. For coherence, unlike all other light sources, a LD light source produces light waves that are all in phase, e.g., a coherent light having waves with crests and troughs all line up at the same time, while a LED light source produces conventional, incoherent light. As for bandwidth, both LED and LD light sources are both monochromatic, producing a single color. However, the LD light source may produce a single wavelength, while the LED light source may produce a very narrow range of light centered on one particular wavelength, e.g., a spread around the one particular wavelength. Further, for direction, the LD light is collimated, that is, it spreads out very little on its own, keeping a narrow beam, while the LED light may have a spread-out wider beam. If needed, lenses can be used to focus light to a pinpoint or spread it into a broad angle.

Typically, the two LED and LD light sources may be compared as follows in the table below.

TABLE

Comparison of LED and LD Sources

| specification | Light Emitting Diode | Laser Diode |
| --- | --- | --- |
| Output power | Linearly proportional to drive current | Proportional to current above the threshold |
| Current | Drive Current (50 to 100 mA) (Peak) | Threshold current (5 to 40 mA) |
| Coupled power | Moderate | High |
| Speed | Slower | Faster |
| Output pattern | Higher | Lower |
| Fiber Type | Multimode only | Single mode and multi-mode |
| Ease of use | Easier | Harder |
| Lifetime | Longer | Long |
| Spectral width | Wider, 25 to 100 nm (10 to 50 THz) | Narrower, $<10^{-5}$ to 5 nm ($<1$ MHz to 2 MHz) |
| Modulation Bandwidth | Moderate, Tens of KHz to tens of MHz | High, Tens of MHz to tens of GHz |
| Available Wavelength | 0.66 to 1.65 mm | 0.78 to 1.65 mm |
| E/O Conversion Efficiency | 10 to 20% | 30 to 70% |
| Cost | Low | Moderate to High |

Depending upon the particular characteristics of the contaminants or materials for detection using the present technology, various combinations of the LED and LD sources may be used for target detection and/or measurement in the fluid flowing in the flow tube.

As another embodiment of the sensor unit (200), an electrical conductivity sensor (230) may be used to measure the contamination of the fluid flowing through the flow tube (100) with hazardous materials, such as heavy metals, using the sensor (239) with electrode or electromagnetic induction coil. As illustrated in FIGS. 4(a) and 4(b), the electrical conductivity sensor (230) may include electrodes (239) such as an anode (233) and a cathode (235) installed in a manner diametrically opposite to the flow tube (100); and an electrical conductivity meter (231) that electrically connects the electrodes (239).

In this regard, the electrodes (239) may be formed with two or four conductive materials (metal, graphite, etc.). The electrical conductivity sensor (230) assesses the fluid flowing through the flow tube (100), using the electrodes (239), to determine whether it is contaminated with hazardous materials, such as heavy metals, or not.

More specifically, the anode (233) and the cathode (235) installed diametrically opposite to the flow tube (100) are used to detect the changes in the electrical conductivity meter (231), which is electrically connected to the electrodes (239), in cases where hazardous materials are mixed in the fluid. The electrical conductivity meter (231) may be configured to measure a voltage (or current) across the electrodes. When a voltage is applied to the electrodes, a current will flow between the two electrodes and its current intensity depends on the conductivity of electricity, by the following expression:

$$R(\Omega) = (\rho \cdot l)/A,$$

$$L = 1/R = (A/l) \cdot K$$

where R is resistance ($\Omega$), $\rho$ is resistivity ($\Omega \cdot cm$), l is distance between of two electrodes (cm), and A is area ($cm^2$), $K(=1/\rho)$ is specific conductivity (mho·cm), and L is conductivity of electricity or electric conductivity.

The measured voltage (or current) across the electrodes may then be compared and used to determine the content of the metallic components based on predetermined profiles of the electric characteristics of the metallic components.

Alternatively, the conductivity of electricity may be measured indirectly by using an electromagnetic induction type technique. By way of example, the measurement of conductivity of inductive type may be based on Faraday's electromagnetic induction as follows:

$$e = N\frac{d\Phi}{dt}$$

where e is electromotive force (V), N is a number of coils wound, and Φ is a magnetic flux density (weber).

In the example, an electric conductivity sensor of electromagnetic induction type may consist of an induced current generator, a first coil, a second coil, and a current receiver. By means of the induction, the current intensity will be transferred from the first coil to the second coil. The current intensity transferred from the first coil to the second coil will depend on the conductivity of a medium, such as a solution. Also, an induced voltage is proportional to the number of windings on the first coil and the second coil. It is noted that when the transferred electric voltage to the second coil is the same, an output current at the second coil is related to a thickness of coil (electric resistance) at the second coil. As the inducted current from the first coil to the second coil is changed by the conductivity of the medium, e.g., the solution, the conductivity of electricity may be determined by measuring the induced current at the second coil.

In another implementation, an electrochemical or voltammetry analysis may be used to obtain predetermined profiles of the electric characteristics of the metallic components in water. That is, in the implementation, a working electrode, a counter electrode, and a reference electrode may be used to determine the electric profiles of the metallic components in water. Voltammetry provides different profiles of current as a function of applied potential between the electrodes, e.g., as the potential is varied the actual current value is measured as dependent variable and plotted. In the example, the working electrode comes in contact with the water containing metallic components, applies the desired potential to facilitate the transfer of charge to and from the water, and a second electrode (the counter electrode or the reference electrode) acts as the other half of a cell. The reference electrode has a known potential with which the potential of the working electrode is determined, and acts as reference in measuring and controlling the working electrode's potential. The counter electrode passes the current needed to balance the current observed at the working electrode. The ions of metallic components may be oxidized or reduced onto the working electrode during a stripping step. The current is measured during the stripping step and analyzed against the known electric profiles of the metallic components present in the water.

Additionally, the electrical conductivity meter (231) may be configured to be viewed directly from the outside so that the user can check whether the fluid is contaminated or not, and the measurement data obtained from the electrical conductivity meter (231) may be transmitted from a control unit (240) to a display unit (410) (as shown in FIGS. 5a and 5b), allowing the user to check the contamination level through the display unit (410).

Figure 8A:
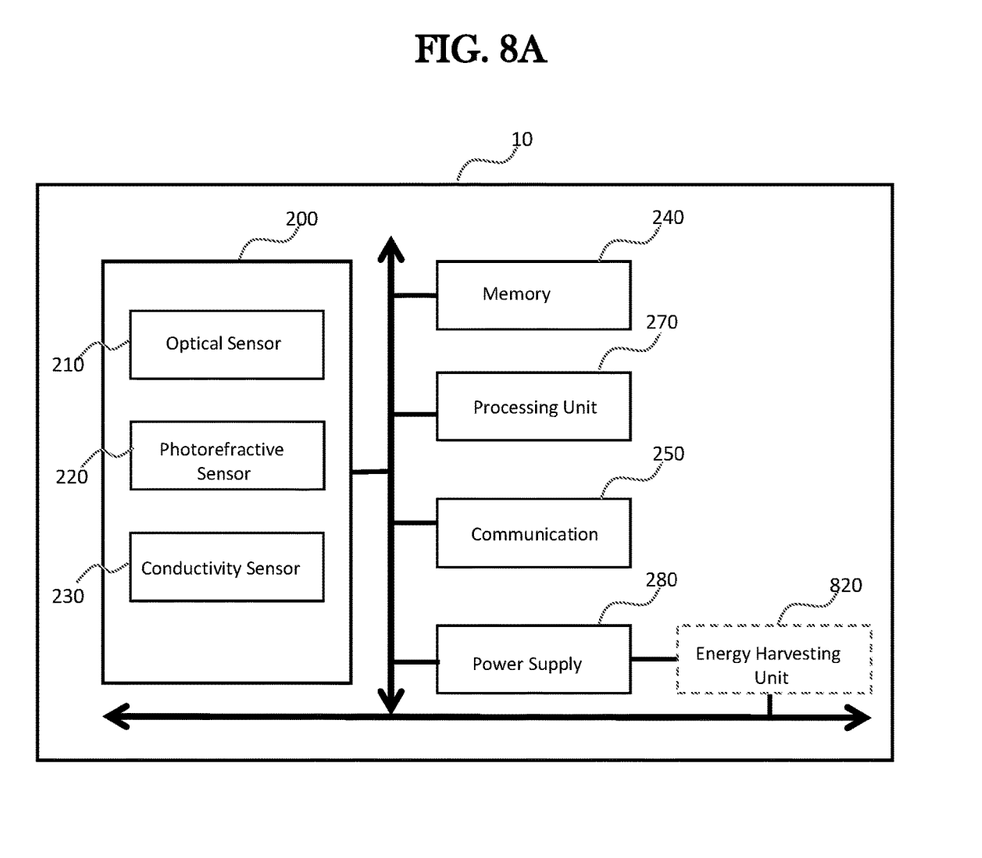
FIGS. 8A and 8B illustrate another embodiment in an aspect of the present disclosure.

In the example, the embodiment of the display unit (410) is shown to be part of the base body (400), but may not be limited thereto. The display unit (410) may be on a remote device (e.g., a smart device 30 as shown in FIG. 7) or at a location, e.g., a smart computing device, a smart phone, a tablet, a PC, a laptop, or the like, which is capable of communicating with a communication unit of the present technology (e.g., a communication unit 250 as shown in FIGS. 7 and 8A). The communication may be done via a variety of communications technologies including but not limited to near-field communication, radio frequency communication, Bluetooth, infrared communications, wifi, or any other short and/or long range wireless communication technologies.

The display unit (410) or the like may provide the user or personnel with certain information as to whether the fluid (e.g., water) flowing through the flow tube (100) is contaminated or not, and if contaminated, then a level of detected contamination in the fluid by the present technology.

Further, in the example, the sensor unit (200) is configured to include the optical sensor (210), the photorefractive sensor (220), and the electrical conductivity sensor (230), as shown in FIGS. 1, 7 and 8A, however, the embodiment of the sensor unit (200) may not be limited thereto. In an aspect of the present disclosure, each of the above sensors may be used alone or in combination according to the user's choice.

In accordance with an aspect of the present disclosure, the sensor unit (200) may be configured to detect and/or measure not only biological contamination, but also contamination with other solutions and various heavy metals in water flowing through the flow tube and the two adjoining pipes, and alert the user of any contamination in the water.

Referring back to FIG. 1, the sensor unit (200) includes a base body (400) and the display unit (410). The base body (400) of the sensor unit (200) may include a cylindrical shape, within which a storage space (420) is formed, and may be partially transparent to provide a direct view from the outside. A control unit (240) and the display unit (410) may be embedded onto the base body (400) to enable the handling of the sensor installed in the storage space (420) and for the purpose of a direct status monitoring.

Also, the apparatus or device (10) for detecting one or more contaminants and/or measuring water quality may be coupled to the adjacent pipes (1) by means of various types of coupling unit (300).

As an example of the coupling unit (300), the apparatus or device may be coupled to the adjacent pipes (1) by means of welding, riveting, or using various connectors.

In FIGS. 5a and 5b, an exemplary embodiment of the coupling unit (300) of the present disclosure is described.

As illustrated in FIG. 5a, a coupling unit (500) according to the embodiment of the present disclosure may include the first and second flanges (501, 503) that fasten the adjacent pipes (1) to the two ends of the flow tube (100) on the upper and lower sides, respectively; fasteners (505) that fasten the first and second flanges (501, 503); and a packing member (507) provided within the flange for fluid leakage prevention.

The first and second flanges (501, 503) fasten the pipe (1a) and the flow tube (100) together by enclosing the outer surface of the pipe (1a) and the flow tube (100) at both ends in a manner that the semicircle ring-shaped first flange (501) fastens the pipe (1a) and the flow tube (100) together on the upper side, and the semicircle ring-shaped second flange (503) fastens the pipe (1a) and the flow tube (100) together on the lower side.

Additionally, the fastener (505) may be used to fasten the first and second flanges (501, 503). For example, bolt (505a) and nut (505b) may be used for fastening in the embodiment shown in FIG. 5a, but the first and second flanges (501, 503) may be welded or fastened by various other fastening methods as well.

Here, in the example, when the first and second flanges (501, 503) are fastened together, a ring-shaped packing member (307) is provided within the flange to prevent fluid leakage through the gap between the adjacent pipes (1) and the flow tube (100).

In the coupling unit (500), coupling grooves (1*c*, 101) can be carved along the outer surface of the opening of the pipe (1*a*) and that of the flow tube (100), on which the first and second flanges (501, 503) are fastened together, in order to further increase the coupling force between pipe (1*a*) and flow tube (100).

Also, coupling projections may be formed in the first and second flanges (501, 503) to fit into the coupling grooves (1*c*, 101) so that pipe (1*a*) and flow tube (100) can be easily joined under increased coupling force.

According to another embodiment of the present technology, as illustrated in FIG. 6, the coupling unit (600) is designed to slide into the flow tube (100). In this embodiment, the coupling unit (600) includes a housing (601) with its ends screwed to the adjacent pipes (1); a latch (610) for preventing the housing (601) from being separated from the flow tube (100); and a packing member (607) provided along the inner surface of the housing (601) to prevent fluid leakage.

First, the housing (601) is designed to have a circumference exceeding that of the adjacent pipes (1) so that it can enclose the opening of the adjacent pipes (1) in the form of a ring and be screwed to the screw thread of the outer circumferential surface of the opening of adjacent pipes (1).

In this embodiment, the latch (610) may play the function of preventing the housing (601) from being separated from the flow tube (100) while allowing it to slide along.

To achieve this, a projection (102) is formed, which protrudes to the outer surface of the flow tube (100) coupled to the opening of the pipe (1*a*), and a lock step (611) is formed inside the housing (601) to match the projection (102).

Thus equipped, the housing (601) can slide along the outer surface of the flow tube (100), and is prevented from being separated from the flow tube (100) by the latch (610).

Furthermore, the housing (600) may be formed in combination with the flow tube (100), whereby it can be combined by means of a partial structure designed to facilitate the coupling of the lock step (611) and the projection (102).

Another embodiment of the present disclosure is described below. In an aspect of the present disclosure, the device or apparatus 10 for detecting one or more contaminants and/or measuring water quality by detecting presence of contaminants in water flowing in a pipe is shown in FIG. 7. As illustrated in FIG. 7, the device or apparatus 10 includes the above-described components, including a control unit (240) and a communication unit (250).

In the example, the control unit (240) may be coupled to a display unit (410) that is configured to receive the water quality measurement data of the fluid flowing through the flow tube (100) from the optical sensor (210), photorefractive sensor (220), and electrical conductivity sensor (230), and to transmit the data received to the communication unit (250) for display to a user.

Here, the display unit (410) is configured to display the transmitted data on the screen for the user for monitoring. The user can also operate the sensor through remote control. However, in another implementation, the device or apparatus 10 may not include the display unit (410) and the display unit (410) may be located at a remote device such as a user's device or computer console.

Therefore, the communication unit (250) that receives the data transmitted from the control unit (240) may be configured to wirelessly communication with an external smart device (30) for display to the user. Here, the smart device (30) may include any smartphone, smart pad, tablet PC, etc., not limited to any particular device.

In the example, the communication unit (250) enables the user or administrator to easily monitor the water quality measurement data obtained with the device for detecting one or more contaminants and/or measuring water quality (10') through the integrated communication using an application software of a smart device (30).

Figure 8B:
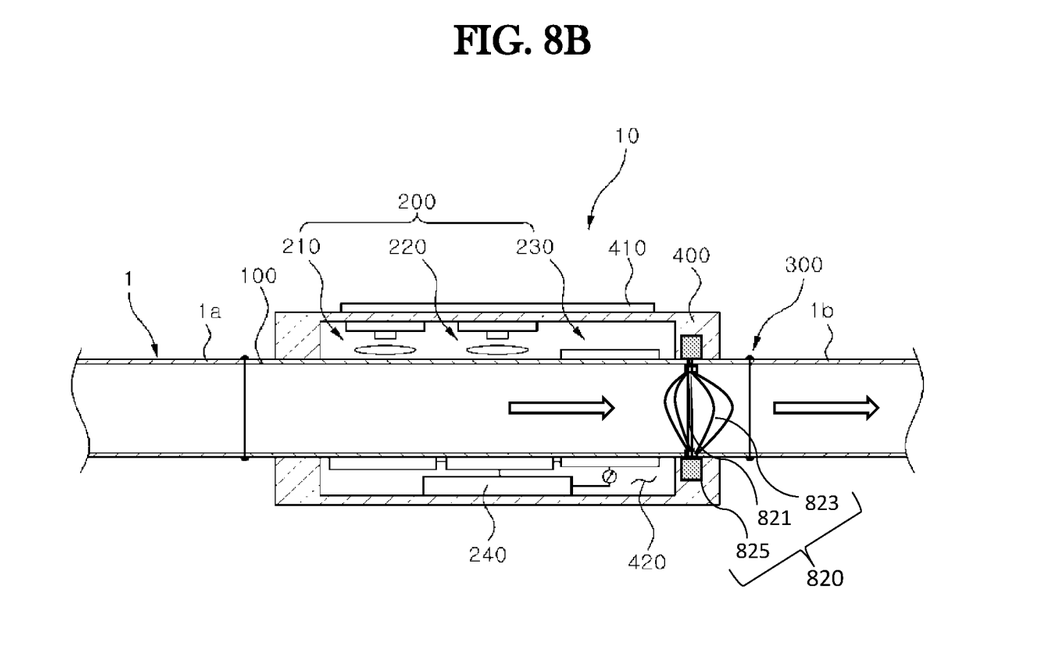

FIG. 8A illustrates another example of an embodiment in accordance with an aspect of the present disclosure. The apparatus (10) for detecting one or more contaminants and/or measuring water quality by detecting presence of the one or more contaminants in water flowing in the flow tube (100) may include a sensor system (200), a processing unit (270) coupled to one or more memories (240), a communication unit (250), and a power supply (280). In the example, the power supply (280) may include one or more batteries or a rechargeable energy storage unit. Further, in another aspect of the present disclosure, the power supply (280) may be coupled to an energy (or power) harvesting unit (820). The energy harvesting unit (820) may be implemented in various forms. In the example as shown in FIG. 8B, an example of the energy harvesting unit (820) is implemented in the form of an electric energy harvesting unit based on movements of fluid or water in the flow tube.

In one implementation, the energy harvesting unit (820) disposed in the base body (400) of the apparatus (10) may include a shaft (821), turbine blades (823), and a power generation unit (825). The energy harvesting unit (820) generates power or electricity based on a commonly known technology such as turbine based power generation. That is, as the fluid or water passes through the flow tube (100) from the left to the right, as shown in FIG. 8B, the turbine blades rotate around the shaft (821) and in turn the rotary motion or kinetic energy of the shaft (821) is transformed into electric energy or power by the power generation unit (825), which may be implemented using one or more rotors and stators in various forms. The power or electricity generated by the power generation unit (825) is then used to either charge the power supply 280 or directly supply electric power to other electronics devices for operation of the apparatus (10). As such, in an aspect of the present disclosure, the apparatus (10) may operate based on self-generated power without replacements of on-board batteries, providing power to various sensing systems such as optical sensor (210), photorefractive sensor (220), conductivity sensor (203), other electronics, etc.

Further, the evaluation of water quality may be determined based on a combination of measurements with optical sensor(s), optical refractive sensor(s), and/or electricity conductivity sensor(s). For example, the measurement from the optical sensor(s) indicate presence of biological materials, such as micro organisms in the water compared to a case when there is no biological materials, such as micro organisms. The measurement from the optical refractive sensor(s) indicates whether or not there is a solution (e.g., organic or inorganic solvents dissolved) other than water. The measurement from the electricity conductivity sensor(s) indicates presence of metallic ion compound(s) in the water. In an aspect of the present disclosure, for each type of sensors, one or more thresholds may be predetermined and used for detecting and determining a quality level of the water in the flow tube, which may be determined or adjusted on other environment factors such as types of sensors, flow tube's diameter, transparency, thickness, power of light, and light source, etc.

As explained above, according to an exemplary embodiment of the present technology, the present disclosure offers user convenience because it can measure water quality after being installed in a place selected by the user without the need of sampling the fluid flowing through the pipe of a system such as tap water, water purifier, drinking water storage facility, or water intake facility.

Furthermore, it enables the monitoring of the contamination status of the fluid flowing through the pipe any time chosen by the user because the water quality of the fluid flowing through the pipe can be measured continuously or intermittently through the sensor unit.

The present disclosure also provides safety and convenience owing to its easy and safe handling without using any tools because it can be easily coupled to and detached from the adjacent pipes through a simple fastening method.

While all components constituting some embodiments of the present disclosure have been described as being combined or operating in combination, it is to be understood that the present disclosure is not limited to those embodiments. That is, all those components can be combined for operation, with one or more components selected within the scope of the present disclosure.

Figure 9:
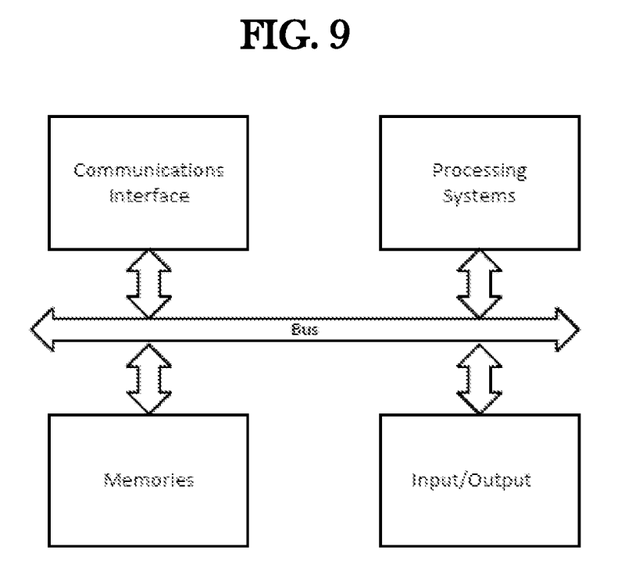
FIG. 9 is a diagram conceptually illustrating a computing architecture in an aspect of the present disclosure.

FIG. 9 shows a diagram illustrating an example of a processing system. The processing system may be included in the device or apparatus including the flow tube. As shown in FIG. 9, a bus may link together various circuits, including one or more processing systems (or processors), one or more memories, one or more communication interfaces, and/or one or more input/output devices. The one or more processing systems may be responsible for managing the bus and general processing, including the execution of software stored on a non-transitory computer-readable medium. Further, the one or more processing systems may include one or more processors, such as microprocessors that interpret and execute instructions. In other implementations, the one or more processing systems may be implemented as or include one or more application specific integrated circuits, field programmable logic arrays, or the like. The software, when executed by the one or more processing systems, may cause the one or more processing systems to perform the various functions described herein for any particular apparatus. The non-transitory computer-readable medium may also be used for storing data that is manipulated by the one or more processing systems when executing software. The one or more memories may include various types of memories, including a random access memory and/or a read only memory, and/or other types of magnetic or optical recording medium and its corresponding device for storing information and/or instructions and/or retrieval thereof. The one or more communication interfaces may also include any transceiver-like mechanism that enables communication with other devices and/or systems. The one or more input/output devices may include devices that permit inputting information and/or outputting information to an operator.

Even though particular combinations of features are disclosed in the specification and/or recited in the claims, these combinations are not intended to limit the disclosure of the present technology. Further, the methods or methodologies for the present technology disclosed herein may be implemented in software, hardware, any combinations of software and hardware, a computer program or firmware incorporated in a computer readable medium for execution by a controller, a processor, a computer, or a processing system that includes one or more processors. Examples of processors include microcontrollers, microprocessors, digital signal processors (DSPs), discrete hardware circuits, gated logic, state machines, programmable logic devices (PLDs), field programmable gate arrays (FPGAs), and other suitable hardware configured to perform various functions described herein. The term "software" as used herein is to be construed broadly to mean any instructions, instruction sets, programs, subprograms, code, program code, software modules, applications, software packages, routines, objects, executables, threads of execution, procedures, functions, etc. including firmware, microcode, middleware, software, hardware description language, or the like.

Also, the term "software" as used herein includes various types of machine instructions including instructions, code, programs, subprograms, software modules, applications, software packages, routines, subroutines, executables, procedures, functions, etc. The software may also refer to general software, firmware, middleware, microcode, hardware description language, or etc. As noted above, the software may be stored on a computer-readable medium.

Examples of a computer-readable medium may include a non-transitory computer-readable medium, such as, by way of example, an optical disk, a magnetic storage device, a digital versatile disk, a flash memory, random access memory (RAM), read only memory (ROM), a register, programmable ROM (PROM), erasable PROM (EPROM), electrically erasable PROM (EEPROM), a removable disk, a flash memory device, and any other suitable medium for storing software that may be accessed and read by a processor or a processing system. It is also appreciated that one skilled in the art will recognize how best to implement the described functionality relating to adding new system functionalities to an existing network element, depending upon a particular application within design constraints.

The term "unit" or "component" as used herein means software, hardware, or any combinations thereof. A unit may be implemented as a software component, a hardware component, or any combinations thereof, including a field programmable gate array (FPGA), logic, logic arrays, application specific integrated circuit (ASIC), digital signal processor (DSP), microcontroller, microprocessor, etc. or any combinations thereof. The unit thus may include software components, task components, processes, procedures, functions, program code, firmware, micro-codes, circuits, data structures, tables, arrays, and variables.

While for the purpose of simplicity the methodologies are described herein as a series of steps or acts, it is to be understood that the claimed subject matter is not limited by the order of steps or acts, as some steps or acts may occur in different orders and/or concurrently with other acts from that shown and described herein. Further, not all illustrated steps or acts may be required to implement various methodologies according to the present technology disclosed herein.

Furthermore, the methodologies disclosed herein and throughout this specification are capable of being stored on an article of manufacture to facilitate transporting and transferring such methodologies to one or more processing systems. The term "article of manufacture" is intended to encompass a computer program accessible from any computer-readable device, carrier, or medium.

A singular form may include a plural form if there is no clearly opposite meaning in the context. Also, as used herein, the article "a" is intended to include one or more items. Further, no element, act, step, or instruction used in the present disclosure should be construed as critical or essential to the present disclosure unless explicitly described as such in the present disclosure. As used herein, except explicitly noted otherwise, the term "comprise" and variations of the term, such as "comprising," "comprises," and "comprised" are not intended to exclude other additives, components, integers or steps. The terms "first," "second,"

and so forth used herein may be used to describe various components, but the components are not limited by the above terms. The above terms are used only to discriminate one component from other components, without departing from the scope of the present disclosure. Also, the term "and/or" as used herein includes a combination of a plurality of associated items or any item of the plurality of associated items. Further, it is noted that when it is described that an element is "coupled" or "connected" to another element, the element may be directly coupled or directly connected to the other element, or the element may be coupled or connected to the other element through a third element. A singular form may include a plural form if there is no clearly opposite meaning in the context.

In the present disclosure, the term "include" or "have" as used herein indicates that a feature, an operation, a component, a step, a number, a part or any combination thereof described herein is present. Further, the term "include" or "have" does not exclude a possibility of presence or addition of one or more other features, operations, components, steps, numbers, parts or combinations. Furthermore, no element, act, step, or instructions used in the present disclosure should be construed as critical or essential to the present disclosure unless explicitly described as such in the present disclosure.

Although the present technology has been illustrated with specific examples described herein for purposes of describing example embodiments, it is appreciated by one skilled in the relevant art that a wide variety of alternate and/or equivalent implementations may be substituted for the specific examples shown and described without departing from the scope of the present disclosure. As such, the present disclosure is intended to cover any adaptations or variations of the examples and/or embodiments shown and described herein, without departing from the spirit and the technical scope of the present disclosure.

What is claimed is:

1. An apparatus for detecting one or more contaminants in water flowing in a pipe, the apparatus comprising:
   a first pipe and a second pipe configured to transport water;
   a sensor assembly including a flow tube disposed between the first pipe and the second pipe joining the two pipes into a continuous section for transporting the water, the flow tube including a plurality of transparent windows, wherein the sensor assembly is configured to include:
   an optical sensor configured to detect one or more biological contaminants in the water flowing inside the flow tube; and
   an electricity conductivity sensor disposed on the flow tube and configured to detect one or more metallic contaminants in the water flowing inside the flow tube;
   wherein the optical sensor of the sensor assembly includes:
   a light source configured to emit light through one of the plurality of transparent windows into the water flowing inside the flow tube; and
   a photodetector configured to receive the emitted light from the light source through one of the plurality of transparent windows, the photodetector disposed and facing the light source inside the flow tube; and
   wherein the electricity conductivity sensor includes:
   a plurality of electrodes disposed inside the flow tube and including an anode and a cathode installed diametrically opposite in the flow tube; and
   an electrical conductivity meter coupled to the plurality of electrodes and configured to measure a voltage or a current across the plurality of electrodes for determining a presence of the one or more metallic components in the water flowing inside the flow tube.

2. The apparatus of claim 1, further comprising one or more coupling units configured to couple the first pipe, the flow tube, and the second pipe into the continuous section for transporting the water.

3. The apparatus of claim 1, wherein the flow tube includes a transparent portion enabling a direct view from outside.

4. The apparatus of claim 1, further comprising an energy harvesting unit configured to generate power from a fluid movement of the water through the flow tube, wherein the energy harvesting unit is configured to supply the generated power to one or more components of the apparatus.

5. The apparatus of claim 4, wherein the energy harvesting unit comprises:
   one or more turbine blades disposed inside the flow tube; and
   a power generation unit coupled to the one or more turbine blades and configured to transform a rotary movement of the one or more turbine blades to electric energy.

6. The apparatus of claim 5, wherein the energy harvesting unit is configured to supply power to the optical sensor and the electrical conductivity sensor for operation.

* * * * *